United States Patent
Lai

(10) Patent No.: US 9,826,612 B2
(45) Date of Patent: Nov. 21, 2017

(54) X-RAY EMISSION DEVICE

(71) Applicant: Wistron Corporation, New Taipei (TW)

(72) Inventor: Chun-Chih Lai, New Taipei (TW)

(73) Assignee: Wistron Corporation, New Taipei (TW)

( * ) Notice: Subject to any disclaimer, the term of this patent is extended or adjusted under 35 U.S.C. 154(b) by 76 days.

(21) Appl. No.: 14/854,047

(22) Filed: Sep. 15, 2015

(65) Prior Publication Data

US 2016/0374187 A1    Dec. 22, 2016

(30) Foreign Application Priority Data

Jun. 18, 2015    (TW) .............................. 104119744 A

(51) Int. Cl.

| *H05G 1/70* | (2006.01) |
|---|---|
| *H05G 1/32* | (2006.01) |
| *G21K 1/06* | (2006.01) |
| *A61B 6/00* | (2006.01) |
| *H05G 1/60* | (2006.01) |

(52) U.S. Cl.
CPC .................. *H05G 1/32* (2013.01); *A61B 6/00* (2013.01); *H05G 1/70* (2013.01); *A61B 6/4007* (2013.01); *G21K 1/065* (2013.01); *H05G 1/60* (2013.01)

(58) Field of Classification Search
CPC .......... A61B 6/4007; H05G 1/36; H05G 1/56; H05G 1/70
See application file for complete search history.

(56) References Cited

U.S. PATENT DOCUMENTS

| 6,208,706 B1* | 3/2001 | Campbell | ................ H05G 1/36 |
|---|---|---|---|
| | | | 378/9 |
| 7,440,547 B2* | 10/2008 | Ishiyama | ............... A61B 6/032 |
| | | | 378/101 |
| 2006/0233297 A1* | 10/2006 | Ishiyama | ............... A61B 6/032 |
| | | | 378/9 |
| 2013/0129038 A1 | 5/2013 | Wang | |
| 2014/0185754 A1 | 7/2014 | Tang | |
| 2015/0223767 A1* | 8/2015 | Sehnert | ..................... A61B 6/06 |
| | | | 378/42 |
| 2016/0374187 A1* | 12/2016 | Lai | ........................... H05G 1/32 |

FOREIGN PATENT DOCUMENTS

| CN | 103901057 A | 7/2014 |
|---|---|---|
| TW | M302049 | 12/2006 |

OTHER PUBLICATIONS

Office action dated Dec. 14, 2016 for TW application No. 104119744, filing date: Jun. 18, 2015, p. 1 line 10~14 and p. 2 line 1~25.

\* cited by examiner

*Primary Examiner* — Thomas R Artman
(74) *Attorney, Agent, or Firm* — Winston Hsu

(57) ABSTRACT

An X-ray emission device for emitting an integrated X-ray beam toward an object is disclosed. The X-ray emission device includes multiple X-ray emission tubes for respectively generating multiple X-rays, and a lens module for guiding the multiple X-rays toward the object to form the integrated X-ray beam.

6 Claims, 12 Drawing Sheets

X-RAY EMISSION DEVICE

BACKGROUND OF THE INVENTION

1. Field of the Invention

The invention is related to an X-ray emission device, and more particularly, to an x-ray emission device replacing a single-tube structure with a multiple-tube structure to reduce heat dissipation requirement.

2. Description of the Prior Art

X-ray is widely employed in medical photography. Via radiation photography, various kinds of diagnostic diagrams can be generated to detect bone pathology, a soft tissue pathology (e.g. pneumonia, lung cancer, and emphysema), etc. With the help of computer technology, X-ray images taken from different aspects can be further synthesized into a three-dimensional image, i.e. computerized tomography. However, an X-ray emission apparatus is frequently troubled by overheating induced by an X-ray emission tube.

Please refer to FIG. 1, which is a schematic diagram of an X-ray emission tube 10 of the prior art. The X-ray emission tube 10 includes an opening 100, a metal anode 110, a cathode 120, a space 130, a cooling layer 140 and a steel case 150. An electronic beam accelerated by a high voltage VH is emitted from the cathode 120, passes through the space 130, and finally collides with the metal anode 110. According to Electromagnetism, electromagnetic waves will be generated when charged particles are accelerated or decelerated. Therefore, since electrons of the electronic beam BE are rapidly stopped by atoms of the metal anode 110, a part of an energy loss of the electrons during the inelastic collision will be converted into an energy of an X-ray BX.

However, inmost experimental results, merely 1% energy of the electronic beam BE is converted into the X-ray BX, and the remaining 99% energy is converted into heat. For that reason, the cooing layer 140 is filled with cooling water or cooling oil to avoid the metal anode 110 from melting. Since the heat dissipation requirement is extremely high, the cooling layer 140 is designed to have a giant size. That is, volume and weight of the X-ray emission tube and its cooling system have to be reduced.

SUMMARY OF THE INVENTION

Therefore, one of the objectives of the present invention is to provide X-ray emission devices with lower heat dissipation requirements.

The present invention discloses an X-ray emission device for emitting an integrated X-ray beam toward an object, the X-ray emission device comprising a plurality of X-ray emission tubes for respectively generating a plurality of X-rays; and a lens module for guiding the plurality of X-rays toward the object to form the integrated X-ray beam.

The present invention further discloses an X-ray emission device for emitting an integrated X-ray beam toward an object, the X-ray emission device comprising a plurality of X-ray emission tubes for respectively generating a plurality of X-rays; a plurality of thermometers, coupled to the plurality of X-ray emission tubes, for respectively measuring a plurality of temperatures of the plurality of X-ray emission tubes; and a controller, coupled to the plurality of thermometers and the plurality of X-ray emission tubes, for controlling duty cycles of the plurality of X-ray emission tubes according to the plurality of temperatures.

The present invention further discloses an X-ray emission device for emitting an integrated X-ray beam toward an object, the X-ray emission device comprising a plurality of X-ray emission tubes for respectively generating a plurality of X-rays; and a driving controller, coupled to the plurality of X-ray emission tubes, for controlling a plurality of driving voltages, a plurality of driving currents or a plurality of exposure periods of the plurality of X-ray emission tubes.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
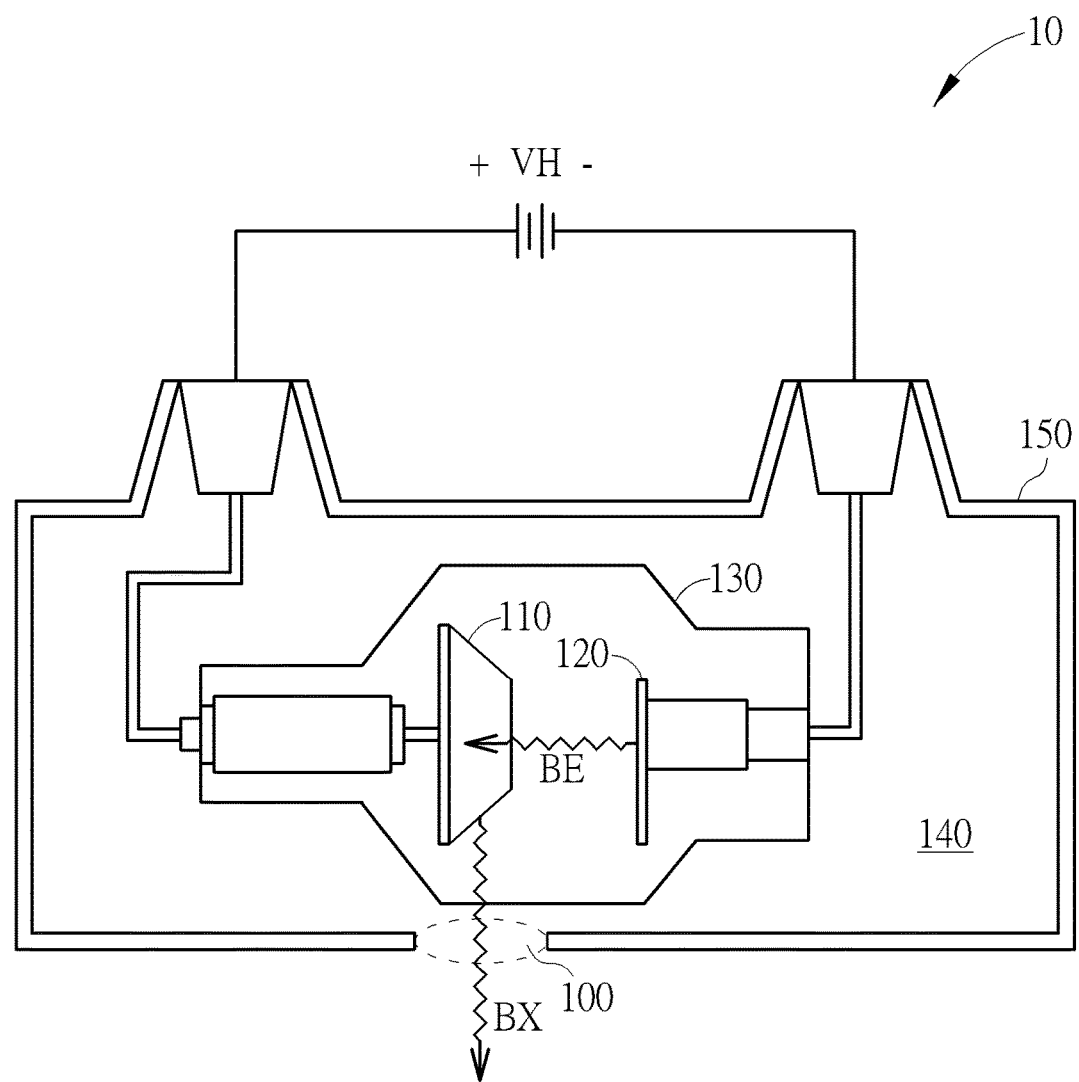
FIG. 1 is a schematic diagram of an X-ray emission tube of the prior art.
Figure 2:
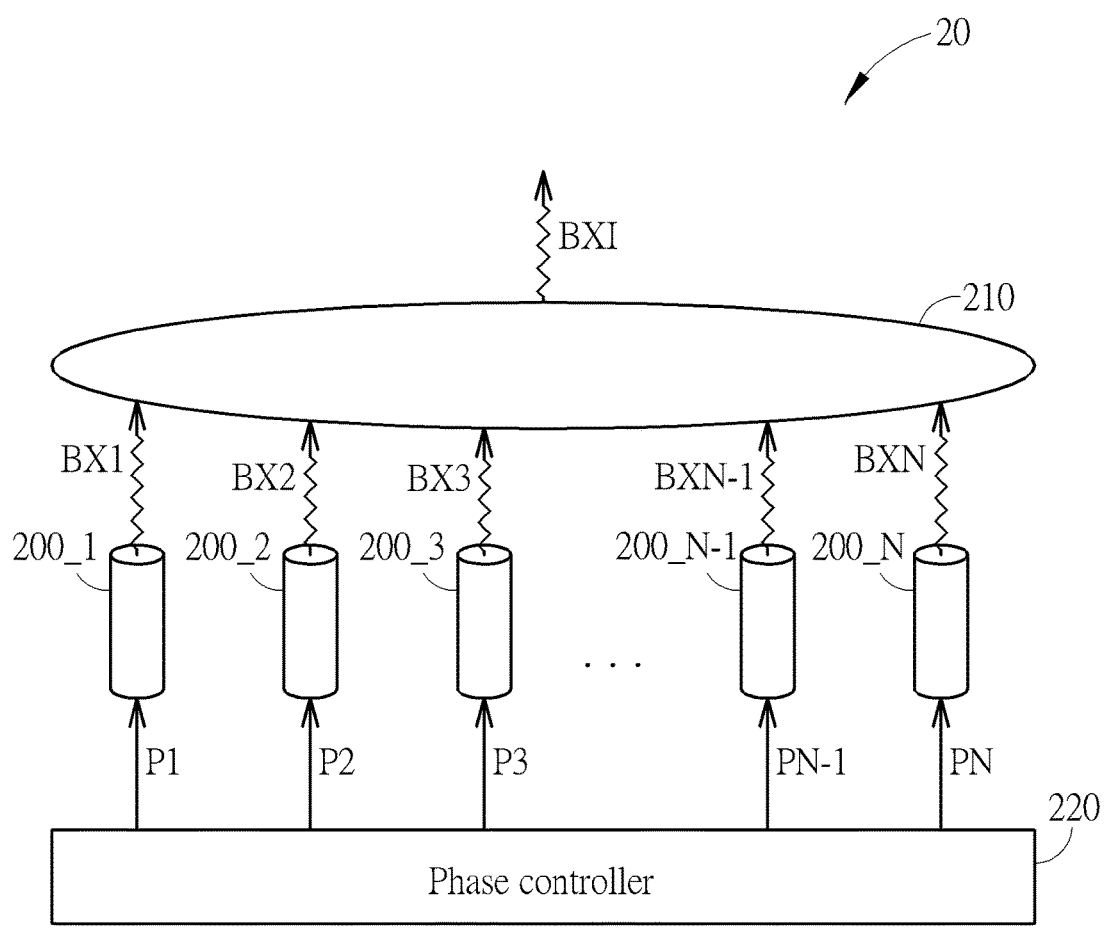
FIG. 2 is a schematic diagram of an X-ray emission device according to an embodiment of the present invention.

Please refer to FIG. 2, which is a schematic diagram of an X-ray emission device 20 according to an embodiment of the present invention. The X-ray emission device 20 is utilized for emitting an integrated X-ray beam BXI toward an object, such as a human bone or a soft tissue. The X-ray emission device 20 includes X-ray emission tubes 200_1-200_N, a lens module 210 and a phase controller 220. The X-ray emission tubes 200_1-200_N are utilized for respectively generating X-rays BX1-BXN. The lens module 210 is utilized for guiding the X-rays BX1-BXN toward the object to form the integrated X-ray beam BXI. The phase controller 220 is utilized for controlling duty cycles of the X-ray emission tubes 200_1-200_N, such that the X-ray emission tubes 200_1-200_N emits the X-rays BX1-BXN in rotation.

Figure 3:
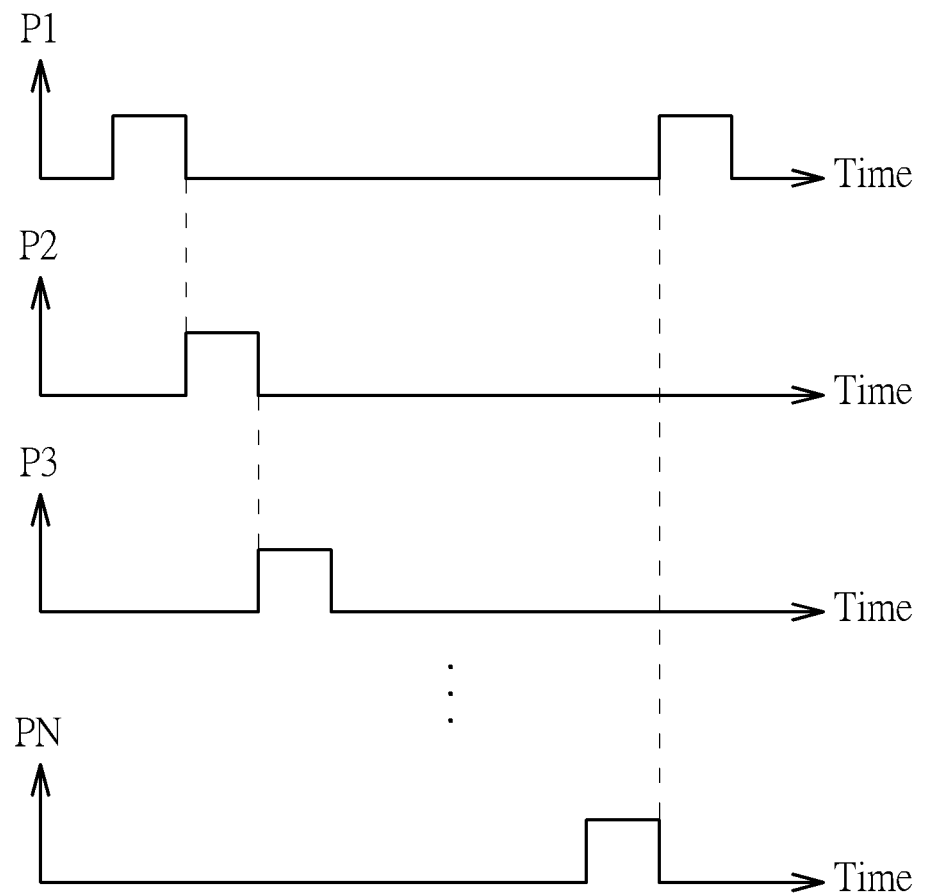
FIG. 3 is a time-variant diagram of phase signals of the X-ray emission device of FIG. 2.
Figure 4A:
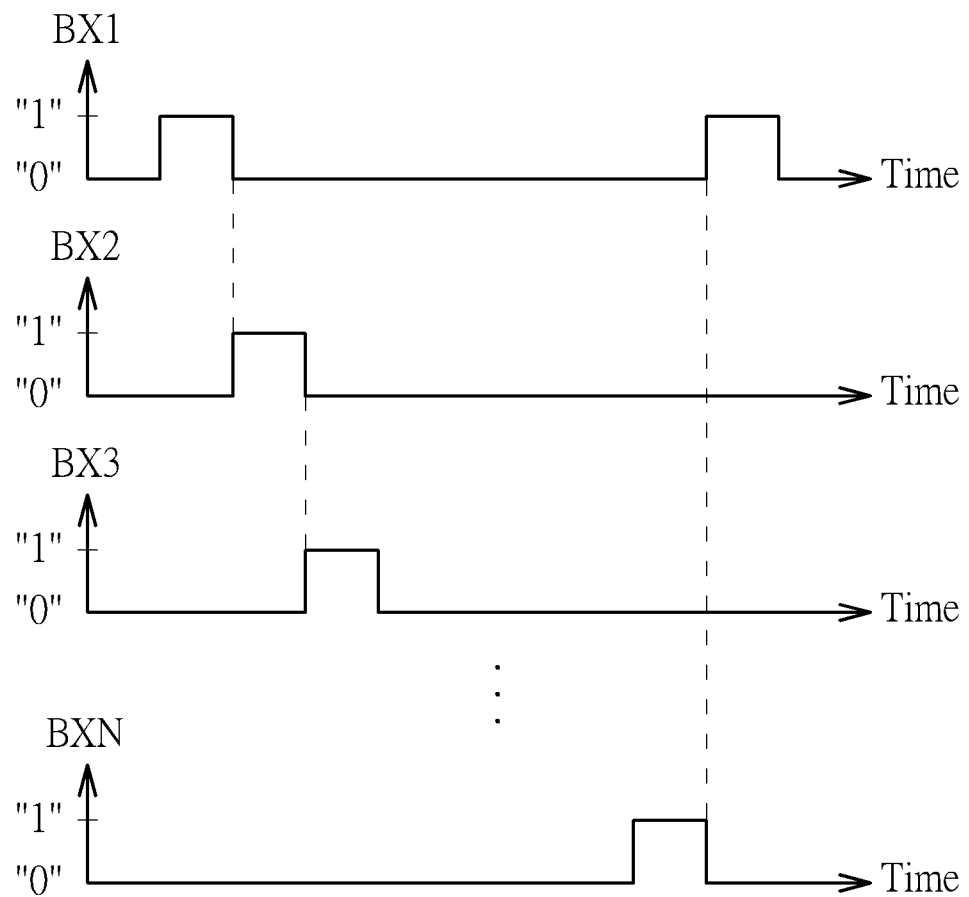
FIG. 4A is a time-variant diagram of X-rays of the X-ray emission device of FIG. 2.

Specifically, the phase controller 220 controls the duty cycles of the X-ray emission tubes 200_1-200_N via phase signals P1-PN. Please refer to FIG. 3, which is a time-variant diagram of the phase signals P1-PN of the X-ray emission device 20. In FIG. 3, when the phase signal P1 is equivalent to logic "1", the X-ray emission tube 200_1 generates the X-ray BX1. Once the phase signal P1 is switched to logic "0", the phase signal P2 is instantly switched from logic "0" to logic "1" to indicate the X-ray emission tube 2002 to generate the X-ray BX2. Based on the same manner, the X-ray emission tubes 200_1-200_N can one by one generate the X-rays BX1-BXN in rotation. Time sequences of the X-rays BX1-BXN are illustrated in FIG. 4A. In FIG. 4A, "1" means the corresponding X-ray exists, and "0" means the corresponding X-ray does not exist. As a result, the X-ray emission tubes 200_1-200_N rotationally, one by one generate the X-rays BX1-BXN. Finally, the lens module 210 guides the X-rays BX1-BXN toward the object.

In other words, workload of the singe X-ray emission tube 10 of the prior art is separated to the multiple X-ray emission tubes 200_1-200_N, so as to reduce required duty cycle for each X-ray emission tube. As a result, since heat dissipated by each of the X-ray emission tubes 200_1-200_N significantly reduces, the X-ray emission device 20 no longer needs a giant cooling system, and can be more easily installed. Also, a manufacturing cost thereof can be reduced.

Figure 4B:
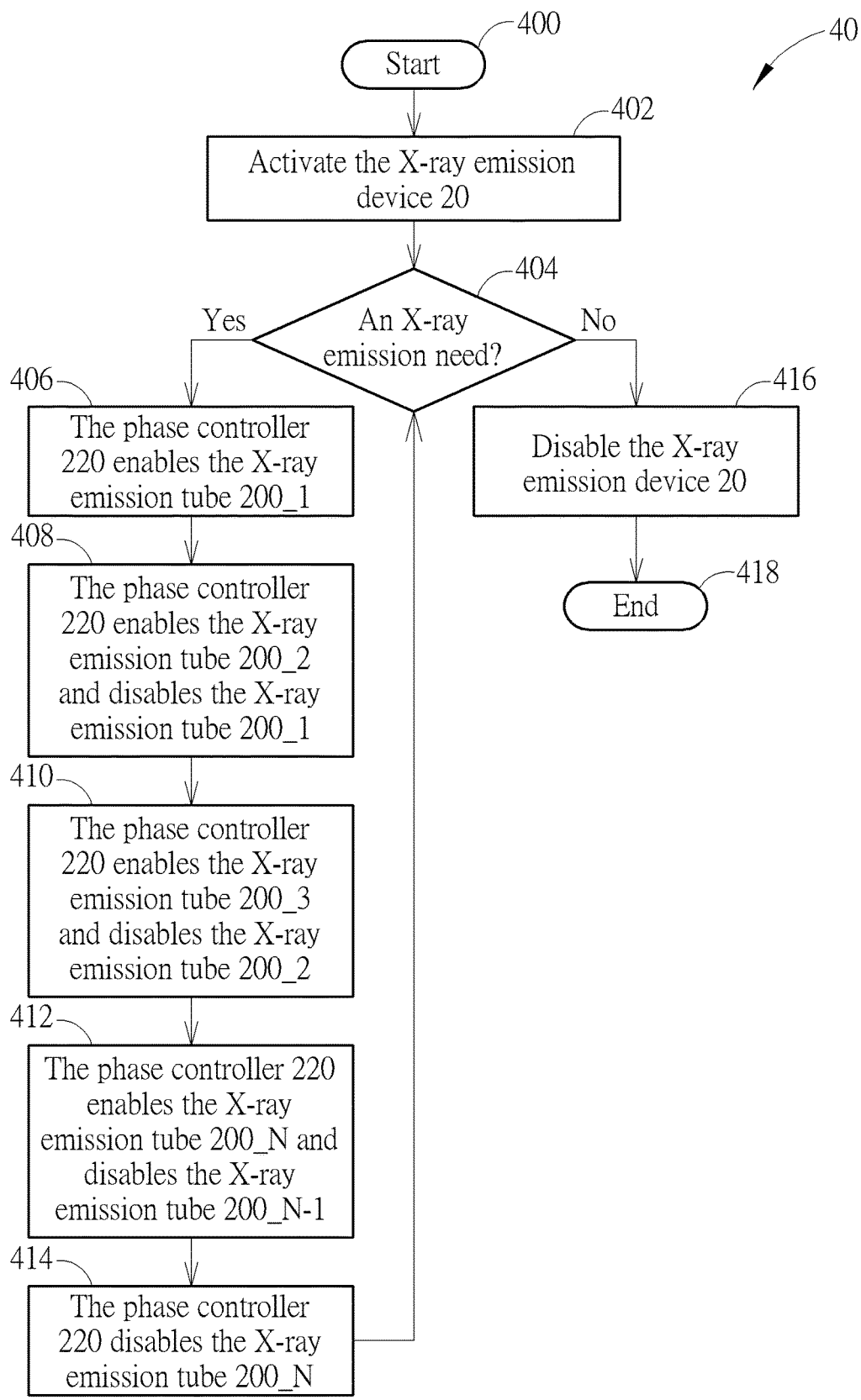
FIG. 4B is a flowchart of a control process of the X-ray emission device of FIG. 2.

Time sequences of FIGS. 3 and 4A can be summarized into a control process 40 as illustrated in FIG. 4B. The control process 40 includes the following steps:

Step 400: Start.

Step 402: Activate the X-ray emission device 20.

Step 404: Determine whether there is an X-ray emission need. If true, proceed to Step 406; else, proceed to Step 416.

Step 406: The phase controller 220 enables the X-ray emission tube 200_1.

Step 408: The phase controller 220 enables the X-ray emission tube 200_2 and disables the X-ray emission tube 200_1.

Step 410: The phase controller 220 enables the X-ray emission tube 200_3 and disables the X-ray emission tube 200_2.

Step 412: The phase controller 220 enables the X-ray emission tube 200_N and disables the X-ray emission tube 200_N–1.

Step 414: The phase controller 220 disables the X-ray emission tube 200_N. Proceed to Step 404.

Step 416: Disable the X-ray emission device 20.

Step 418: End.

Figure 5:
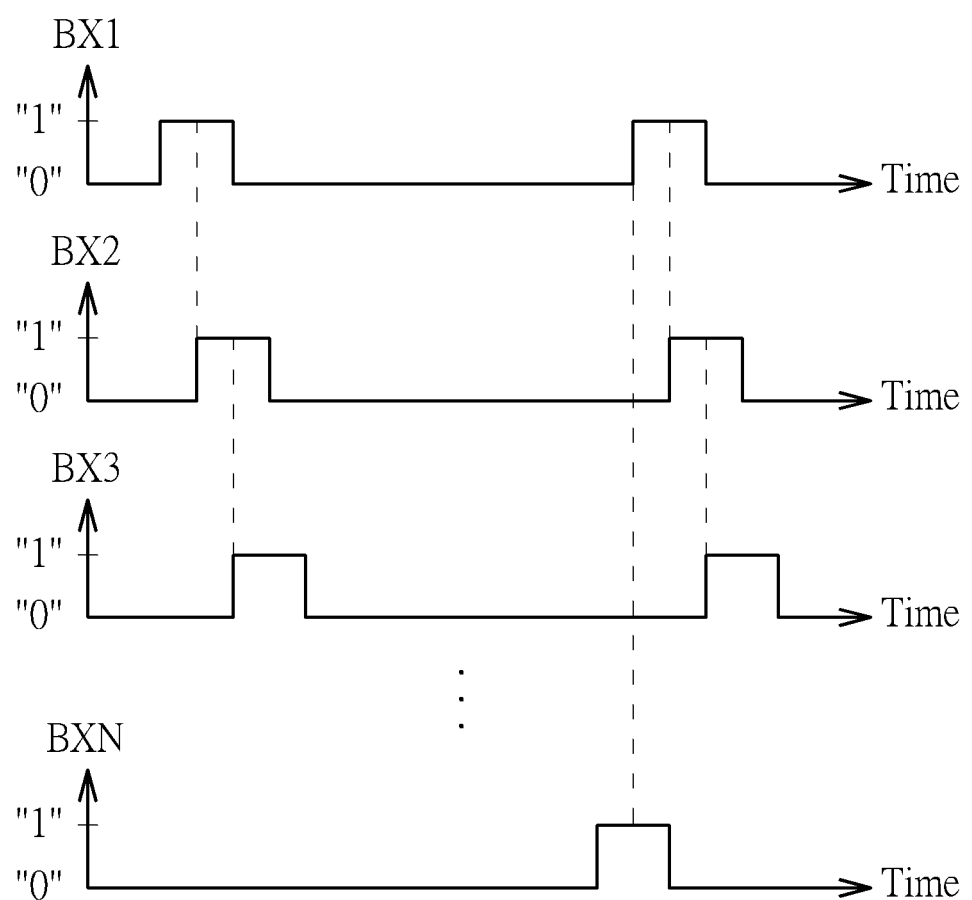
FIG. 5 is a time-variant diagram of X-rays of the X-ray emission device of FIG. 2.
Figure 6:
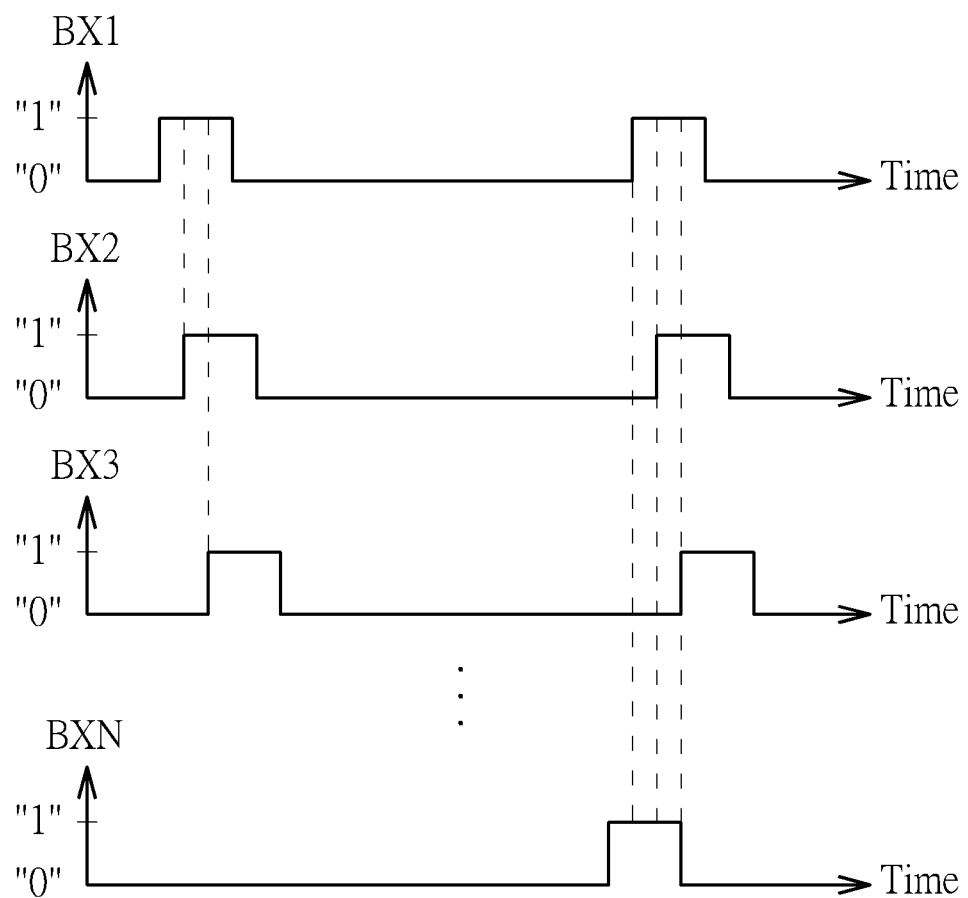
FIG. 6 is a time-variant diagram of X-rays of the X-ray emission device of FIG. 2.

In addition to FIG. 3, the X-ray emission tubes 200_1-200_N also can be controlled by other time sequences. The phase controller 220 can further adjust duty cycles of the phase signals P1-PN based on an illuminance requirement of the integrated X-ray beam BXI. For example, in order to double the illuminance of the integrated X-ray beam BXI, logic "1" periods of the phase signals P1-PN can overlap with each other, such that there will be two X-rays BXx, BXx+1 at the same time, as illustrated in FIG. 5. Similarly, in order to triple the illuminance of the integrated X-ray beam BXI, the phase controller 220 can further arrange the phase signals P1-PN, such that there are three X-rays BXx, BXx+1, BXx+2 at the same time, as illustrate in FIG. 6.

Other than reduction of heat dissipation requirement, another advantage of the present invention is that when one of the X-ray emission tubes malfunctions, the phase controller 220 can increase the duty cycles of the other X-ray emission tubes to maintain the illuminance of the integrated X-ray beam BXI.

In practice, the lens module 210 includes multiple lenses, which are arranged in multiple layers. As such, all of the X-rays BX1-BXN can be guided toward the object. FIG. 2 illustrating a single lens is merely for suggesting the focus function.

Figure 7:
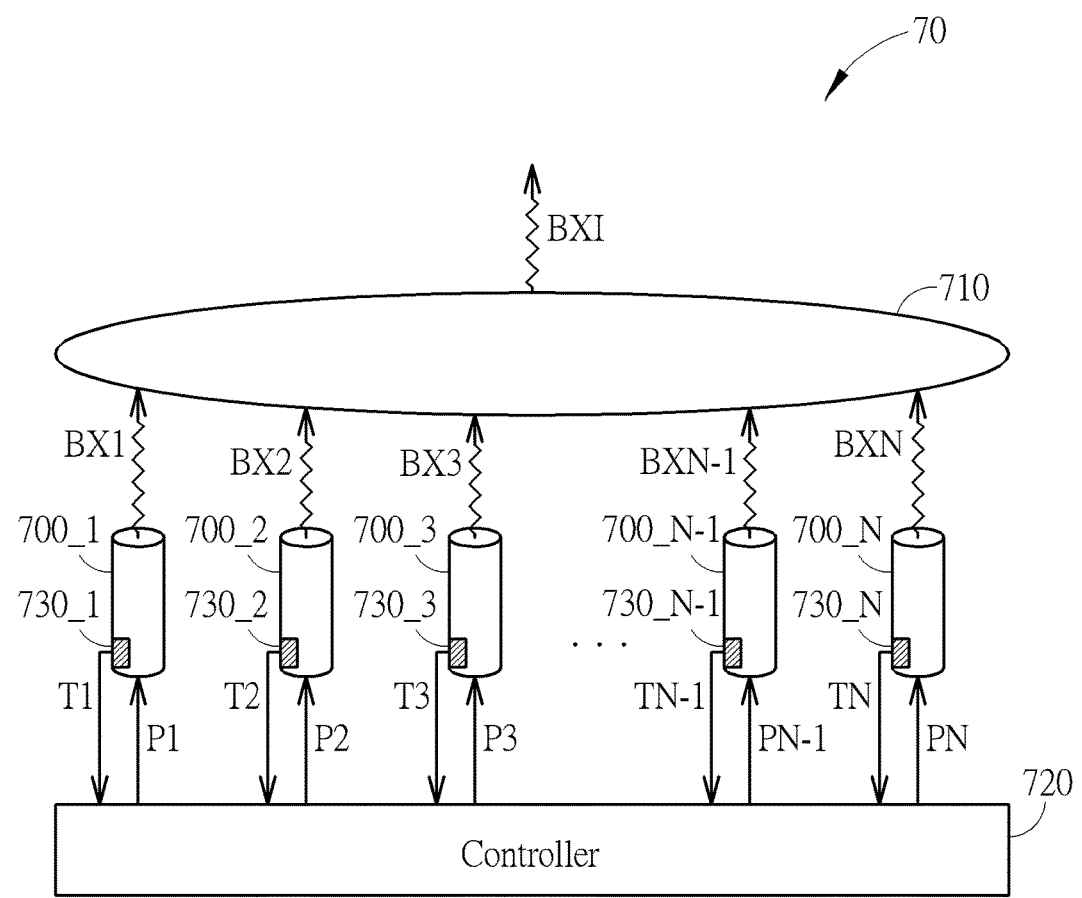
FIG. 7 is a schematic diagram of an X-ray emission device according to another embodiment of the present invention.

Other than rotational emission, the X-ray emission tubes can be further enabled or disabled based on actual temperatures of the X-ray emission tubes according to another embodiment of the present invention. Please refer to FIG. 7, which is a schematic diagram of an X-ray emission device 70 according to another embodiment of the present invention. The X-ray emission device 70 is utilized for emitting an integrated X-ray beam BXI toward an object, and includes X-ray emission tubes 700_1-700_N, a lens module 710, thermometers 730_1-730_N and a controller 720. The X-ray emission tubes 700_1-700_N are utilized for respectively generating X-rays BX1-BXN. The lens module 710 is utilized for guiding the X-rays BX1-BXN toward the object to form the integrated X-ray beam BXI. The thermometers 730_1-730_N are utilized for respectively measuring temperatures T1-TN of the X-ray emission tubes 700_1-700_N. The controller 720 is utilized for controlling duty cycles of the X-ray emission tubes 700_1-700_N via arranging duty cycles of phase signals P1-PN according to the temperatures T1-TN.

Figure 8:
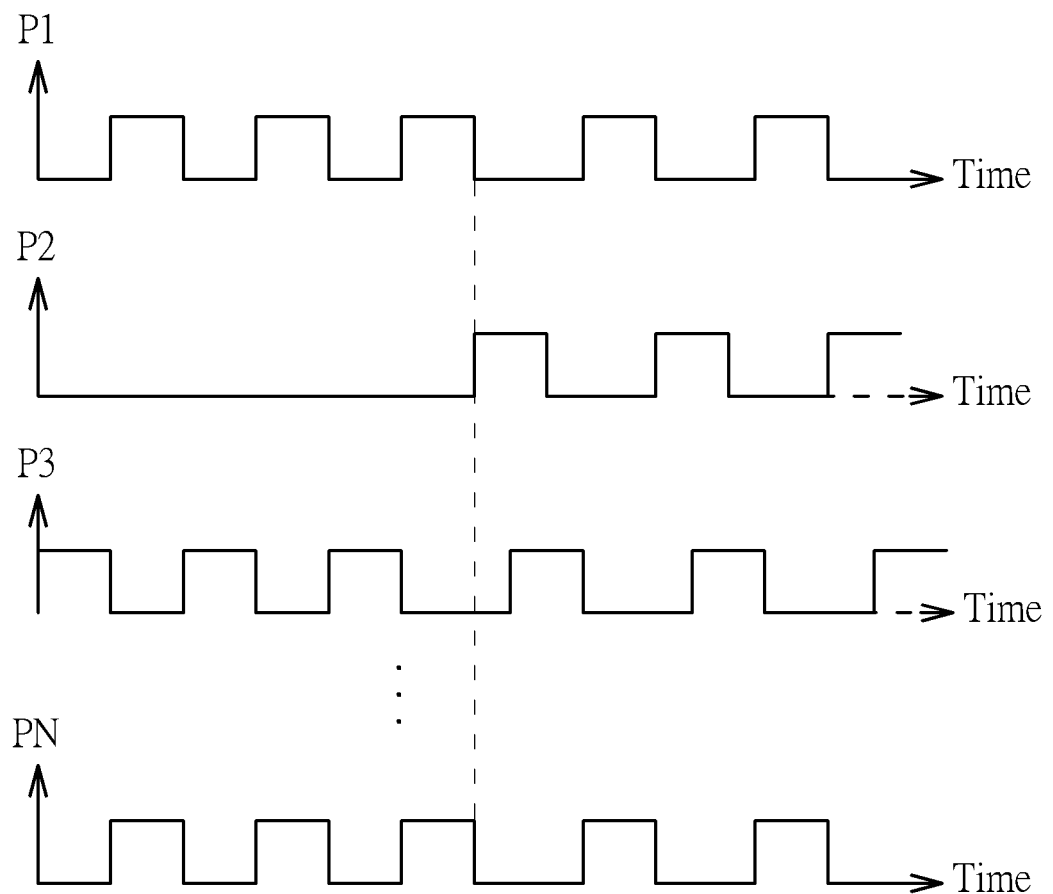
FIG. 8 is a time-variant diagram of phase signals of the X-ray emission device of FIG. 7.
Figure 9:
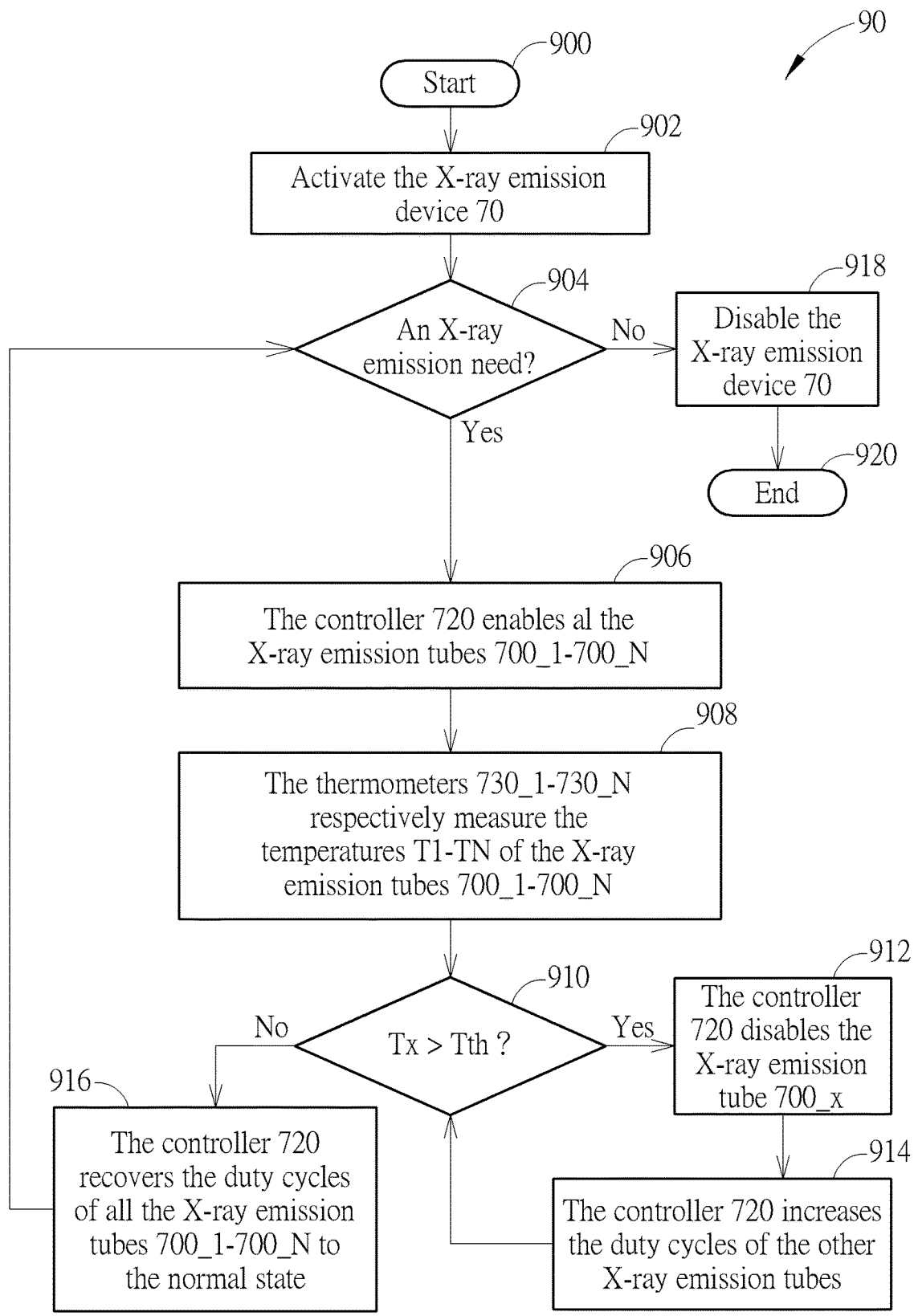
FIG. 9 is a flowchart of a control process of the X-ray emission device of FIG. 7.

For example, please refer to FIG. 8, which is a time-variant diagram of the phase signals P1-PN of the X-ray emission device 70. In FIG. 8, the controller 720 disables the X-ray emission tube 700_2 when the temperature T2 exceeds a temperature threshold Tth, and does not re-enable the X-ray emission tube 7002 until the temperature T2 is less than temperature threshold Tth. In addition, when the X-ray emission tube 700_2 is disabled, the duty cycles of the other X-ray emission tubes 700_1, 700_3-700_N are increased to maintain illuminance of the integrated X-ray beam BXI. The duty cycles of the X-ray emission tubes 700_1, 700_3-700_N will not be arranged to a normal state until the X-ray emission tube 700_2 functions again.

Operations of the X-ray emission device 70 can be summarized into a control process 90, as illustrated in FIG. 90. The control process 90 includes 90 the following steps:

Step 900: Start.

Step 902: Activate the X-ray emission device 70.

Step 904: Determine whether there is an X-ray emission need. If true, proceed to Step 906; else, proceed to Step 918.

Step 906: The controller 720 enables al the X-ray emission tubes 700_1-700_N.

Step 908: The thermometers 730_1-730_N respectively measure the temperatures T1-TN of the X-ray emission tubes 700_1-700_N.

Step 910: If the temperature Tx exceeds the temperature threshold Tth, proceed to Step 912; else, proceed to Step 916.

Step 912: The controller 720 disables the X-ray emission tube 700_x.

Step 914: The controller 720 increases the duty cycles of the other X-ray emission tubes. Proceed to Step 910.

Step 916: The controller 720 recovers the duty cycles of all the X-ray emission tubes 700_1-700_N to the normal state. Proceed to Step 904.

Step 918: Disable the X-ray emission device 70.

Step 920: End.

An advantage of the X-ray emission device 70 and the control process 90 is that all the X-ray emission tubes 700_1-700_N are guarded based on the actual measured temperatures T1-TN, such that all the operating temperatures of the X-ray emission tubes 700_1-700_N will not exceed the temperature threshold Tth, so as to extend an availability period of the X-ray emission device 70. Even though one of the X-ray emission tubes 700_1-700_N malfunctions (damaged or disabled), the other X-ray emission tubes can immediately compensate the vacancy, which means a user does not has to turn off the entire X-ray emission device 70. Operating efficiency thereof is therefore improved.

Figure 10:
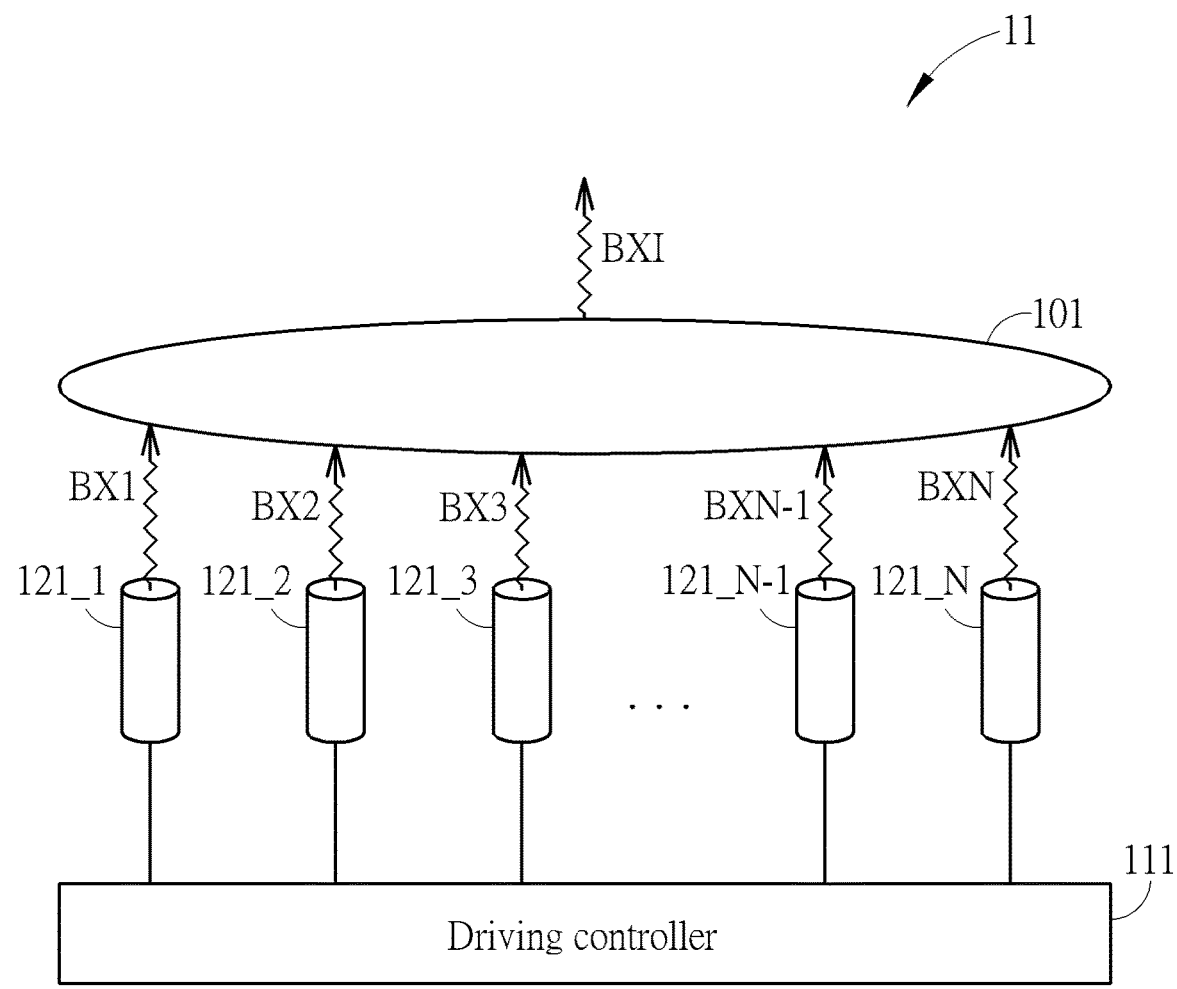
FIG. 10 is a schematic diagram of an X-ray emission device according to another embodiment of the present invention.

Other than the rotational emission and temperature feedback, according to another embodiment of the present invention, a driving condition resulting in overheat can be actively avoided via adjusting intensity, penetration, or illuminance of the integrated X-ray beam, which can be adjusted via arranging driving voltages, driving currents or exposure periods of the X-ray emission tubes. Please refer to FIG. 10, which is a schematic diagram of an X-ray emission device 11 according to another embodiment of the present invention. The X-ray emission device 11 is utilized for emitting an integrated X-ray beam BXI toward an object, and includes X-ray emission tubes 121_1-121_N, a driving controller 111 and a lens module 101. The X-ray emission tubes 121_1-121_N are utilized for respectively generating X-rays BX1-BXN. The driving controller 111 is utilized for controlling driving voltages, driving currents or exposure periods of the X-ray emission tubes 121_1-121_N. The lens module 101 is utilized for guiding the X-rays BX1-BXN toward the object to form the integrated X-ray beam BXI.

According to Electromagnetism, intensity and penetration of the integrated X-ray beam BXI is directly proportional to the driving voltages, and illuminance of the integrated X-ray beam BXI is proportional to the driving currents and the exposure periods. Therefore, the driving controller 111 can arrange the driving voltages of the X-ray emission tubes 121_1-121_N based on an intensity requirement of a penetration requirement of the integrated X-ray beam BXI. Alternatively, according to another embodiment of the present invention, the driving controller 111 can arrange the driving currents or the exposure periods of the X-ray emission tubes 121_1-121_N based on an illuminance requirement of the integrated X-ray beam BXI.

In comparison with the X-ray emission devices 20, 70, the X-ray emission device 11 features the most flexible driving condition since the driving voltages, the driving currents or the exposure periods are actively arranged. In such a situation, in addition to advantages of avoidance of the overheat driving condition and reduction of heat dissipation requirement, the X-ray emission device 11 can handle the most variety of energy requirement of appliance, such as scanning a giant animal or a building.

Figure 11:
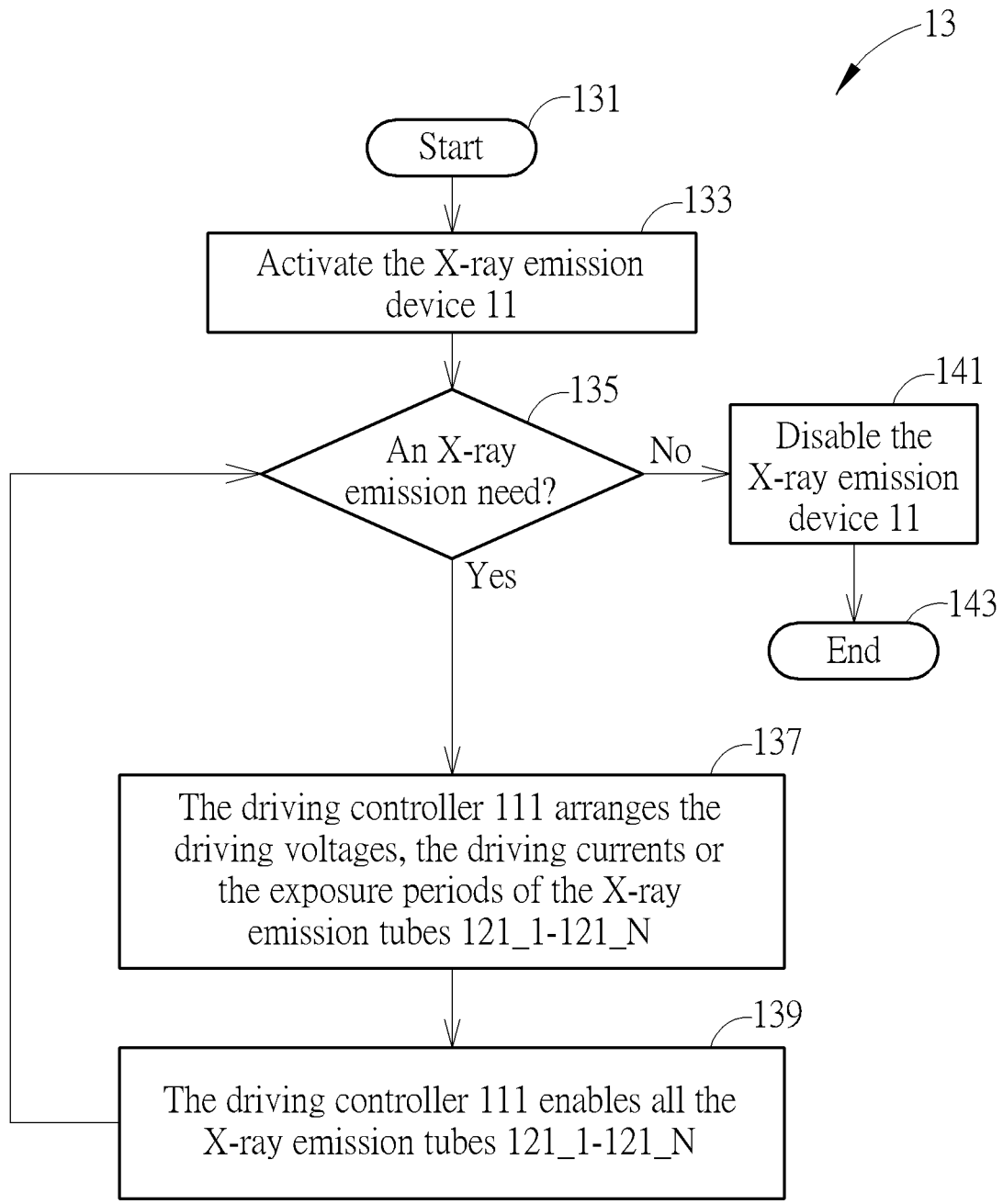
FIG. 11 is a flowchart of a control process of the X-ray emission device of FIG. 10.

Operations of the X-ray emission device 11 can be summarized into a control process 13, as illustrated in FIG. 11. The control process 11 includes the following steps:

Step 131: Start.
Step 133: Activate the X-ray emission device 11.
Step 135: Determine whether there is an X-ray emission need. If true, proceed to Step 137; else, proceed to Step 141.
Step 137: The driving controller 111 arranges the driving voltages, the driving currents or the exposure periods of the X-ray emission tubes 121_1-121_N.
Step 139: The driving controller 111 enables all the X-ray emission tubes 121_1-121_N. Proceed to Step 135.
Step 141: Disable the X-ray emission device 11.
Step 143: End.

In addition, since the X-ray emission device 11 also features the multiple tube structure of the X-ray emission devices 20, 70, when one of the X-ray emission tube 121x malfunctions, the driving controller 111 can further increase duty cycles of the other X-ray emission tubes to maintain the illuminance of the integrated X-ray beam BXI.

To sum up, in order to reduce the size of the cooling system required by the X-ray emission device, the present invention replaces the single-tube structure with the multiple-tube structure, and also features the rotational emission, temperature feedback and driving condition arrangement to reduce heat dissipation and improve the availability period and operating efficiency of the X-ray emission device.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An X-ray emission device for emitting an integrated X-ray beam toward an object, the X-ray emission device comprising:
   a plurality of X-ray emission tubes for respectively generating a plurality of X-rays;
   a lens module for guiding the plurality of X-rays toward the object to form the integrated X-ray beam; and
   a phase controller, coupled to the plurality of X-ray emission tubes, for:
      controlling duty cycles of the plurality of X-ray emission tubes, such that the plurality of X-ray emission tubes emits the plurality of X-rays in rotation; and
      when one of the plurality of X-ray emission tubes malfunctions, increasing the duty cycles of the other X-ray emission tubes to maintain illuminance of the integrated X-ray beam.

2. An X-ray emission device for emitting an integrated X-ray beam toward an object, the X-ray emission device comprising:
   a plurality of X-ray emission tubes for respectively generating a plurality of X-rays;
   a plurality of thermometers, coupled to the plurality of X-ray emission tubes, for respectively measuring a plurality of temperatures of the plurality of X-ray emission tubes;
   a controller, coupled to the plurality of thermometers and the plurality of X-ray emission tubes, for controlling duty cycles of the plurality of X-ray emission tubes according to the plurality of temperatures, such that the plurality of X-ray emission tubes emits the plurality of X-rays in rotation; and
   a lens module for guiding the plurality of X-rays toward the object to form the integrated X-ray beam;
   wherein the controller is further utilized for:
      when the plurality of thermometers indicates that one of the plurality of X-ray emission tubes malfunctions, increasing the duty cycles of the other X-ray emission tubes to maintain illuminance of the integrated X-ray beam.

3. The X-ray emission device of claim 2, wherein the controller is further utilized for disabling one of the plurality of X-ray emission tubes when the corresponding one of the plurality of temperatures exceed a temperature threshold.

4. An X-ray emission device for emitting an integrated X-ray beam toward an object, the X-ray emission device comprising:
   a plurality of X-ray emission tubes for respectively generating a plurality of X-rays; and
   a driving controller, coupled to the plurality of X-ray emission tubes, for controlling a plurality of driving voltages, a plurality of driving currents or a plurality of exposure periods of the plurality of X-ray emission tubes;
   wherein the driving controller is further utilized for:

controlling duty cycles of the plurality of X-ray emission tubes, such that the plurality of X-ray emission tubes emits the plurality of X-rays in rotation; and when one of the plurality of X-ray emission tubes malfunctions, increasing duty cycles of the other X-ray emission tubes to maintain illuminance of the integrated X-ray beam.

5. The X-ray emission device of claim 4, further comprising a lens module for guiding the plurality of X-rays toward the object to form the integrated X-ray beam.

6. The X-ray emission device of claim 5, wherein the driving controller is further utilized for:

controlling the plurality driving voltages according to an intensity requirement or a penetration requirement of the integrated X-ray beam; or controlling the plurality driving currents or the plurality of exposure periods according to an illuminance requirement of the integrated X-ray beam.

\* \* \* \* \*